United States Patent [19]
Mazza

[11] Patent Number: 5,176,157
[45] Date of Patent: Jan. 5, 1993

[54] DEVICE FOR SUPPORTING AND OPERATION A DENTAL FLOSS

[76] Inventor: Mirko Mazza, Marzabotto (Bologna), Italy

[21] Appl. No.: 687,971
[22] Filed: Apr. 19, 1991
[51] Int. Cl.⁵ .............................................. A61C 15/00
[52] U.S. Cl. ..................................... 132/322; 132/325
[58] Field of Search ................. 132/322, 323, 324, 325

[56] References Cited

U.S. PATENT DOCUMENTS

| | | | |
|---|---|---|---|
| 3,667,483 | 6/1972 | McCabe | 132/322 |
| 3,759,274 | 9/1973 | Warner | 132/322 |
| 3,847,167 | 11/1974 | Brien | 132/322 |
| 4,586,521 | 5/1986 | Urso . | |

FOREIGN PATENT DOCUMENTS

| | | | |
|---|---|---|---|
| 9011057 | 10/1990 | PCT Int'l Appl. | 132/322 |
| 9022057 | 11/1990 | PCT Int'l Appl. | 132/322 |

*Primary Examiner*—Cary E. O'Connor
*Attorney, Agent, or Firm*—Darby & Darby

[57] ABSTRACT

The device comprises a rear part containing a motor connected through a series of crown gears and of spindles to a front part shaped complementarily to the rear part, and containing a reel on which a dental floss is wound up, and a truncated-cone element on which the floss winds up as it is used that engages with a spindle driven into continuous rotation, while a small roller with two circumferential races engages with another spindle which is made to oscillate about its vertical axis, so that the dental floss encompasses the small roller and runs between the ends of two branches of a fork and is thus caused to advance swingingly as well as gradually removed after use.

12 Claims, 3 Drawing Sheets

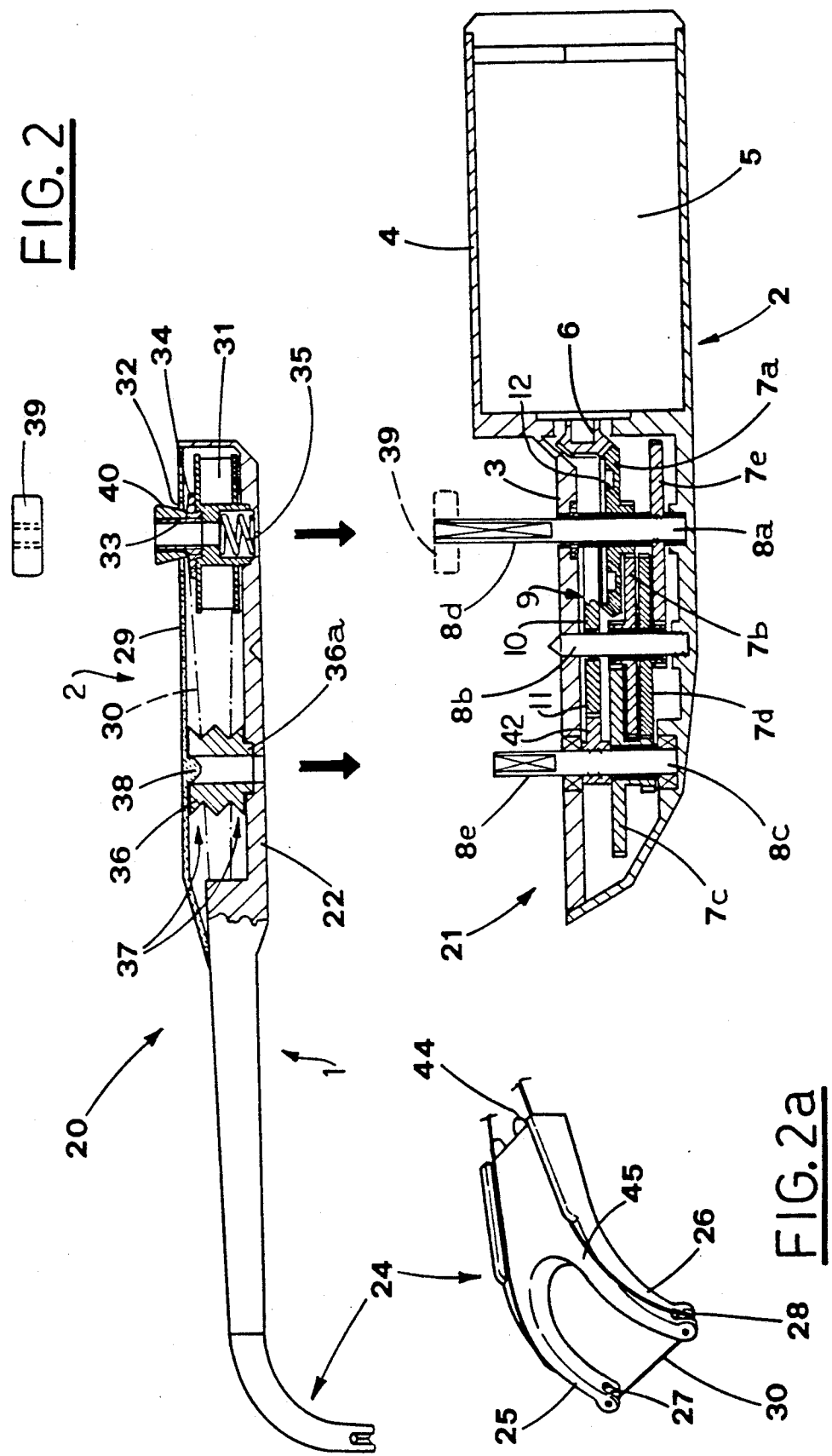

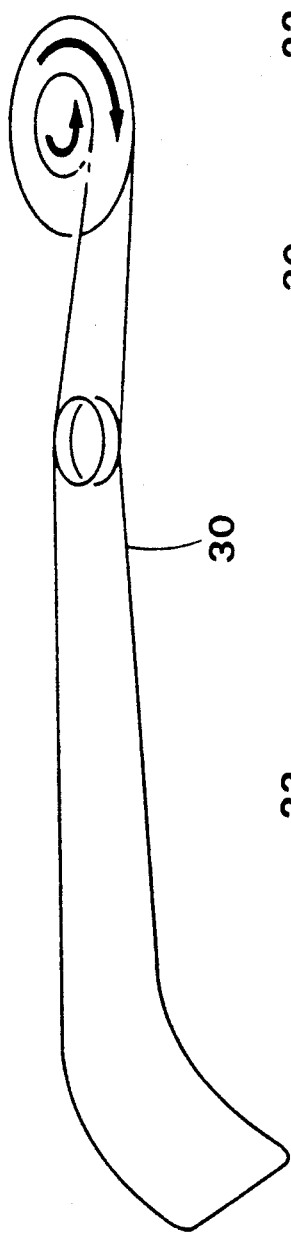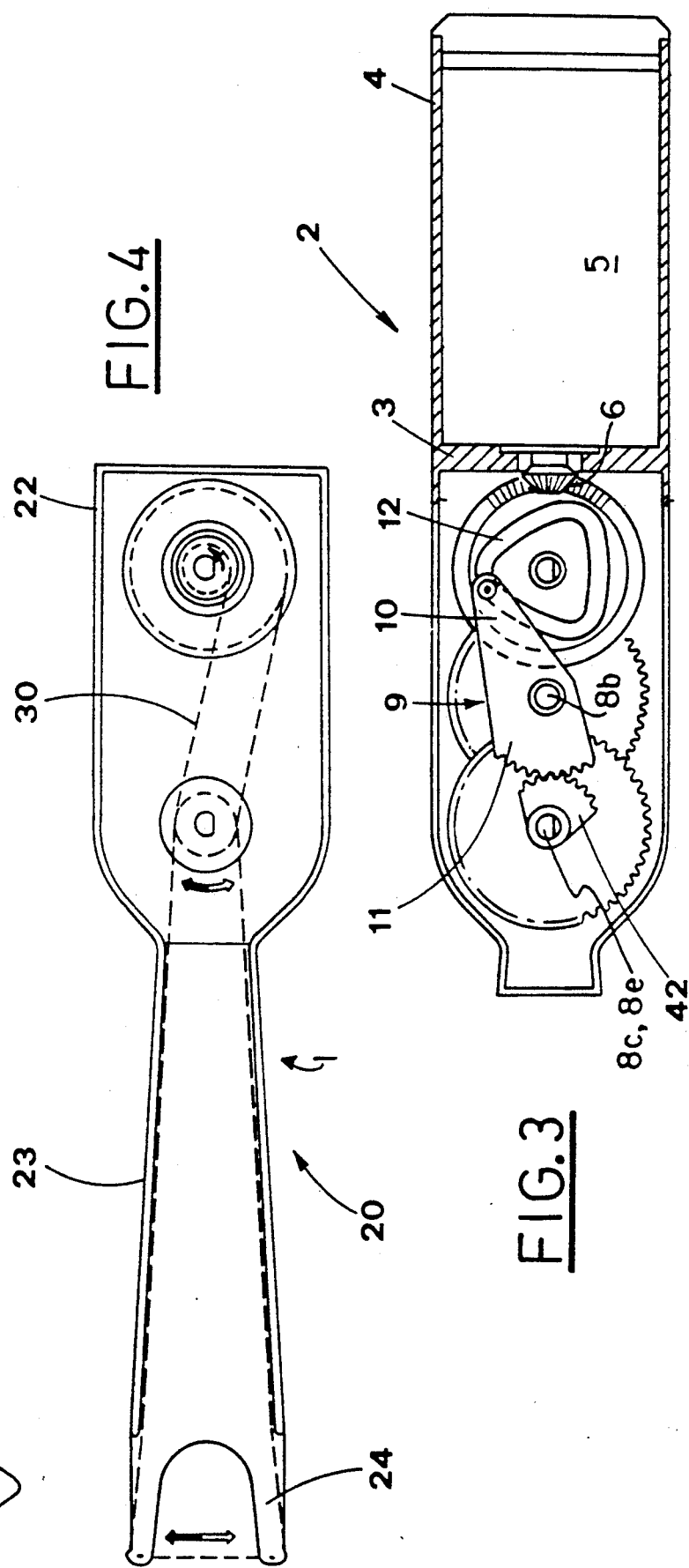

DEVICE FOR SUPPORTING AND OPERATION A DENTAL FLOSS

BACKGROUND OF THE INVENTION

The present invention relates to the technical field concerning the production of articles for oral hygiene.

In particular, the present invention concerns a device suited to support and operate a dental floss.

DESCRIPTION OF THE PRIOR ART

There are some known devices, which allow an improvement in the use of dental floss, both from the practical point of view, i.e. making such use easier, and from the functional point of view, i.e. by trying to make the cleaning action of the dental floss more efficient.

The German patent application DE 3625991, claims an electric device for teeth-cleaning, which supports a dental floss stretched between the ends of the two branches of a fork.

The fork is imparted a swinging motion by an electric motor, so that the floss is made run among the teeth.

It is clear that, though improving the use of the dental floss, such a device presents some drawbacks, both from the hygienic point of view and from the point of view of comfort and pleasure of use.

In fact, every single segment of the dental floss, which is moved alternatively among the teeth, is used repeatedly, until said segment is replaced in its whole length.

Therefore, it is necessary to stop the device periodically and replace the segment of floss.

In any case, the floss is used repeatedly on the same segment, thus with insufficient guarantees in terms of hygiene and functionality.

As far as the pleasure of the use of the device is concerned, the sensation of parts moving inside the oral cavity has a negative impact, and this in some cases may be troublesome or even intolerable.

The German patent application No. 3635608 concerns a device for oral hygiene, wherein there is a dental floss running between the branches of a fork-shaped element. The fork-shaped element is provided with a part shaped like a box, wherein there are a first wind-up reel, a second wind-up reel and a motor.

A suitable length of dental floss is wound up in either sense onto the two wind-up reels which are made to rotate by the motor.

Thus the dental floss, delivered by the first reel, passes through a branch of the fork-shaped element, through the branch of the fork-shaped element located at the opposite side, and from here to the second wind-up reel, and vice versa.

Also in this case, hygienic safety of the use of this item cannot be totally guaranteed, since the dental floss, after having been taken from the first reel and wound on the second reel, is brought back again on the first reel, and in the meantime it is used, and so on, until it is completely replaced.

Therefore, the dental floss carries out multiple runs among the teeth, and this may happen even at intervals of time among the various runs, and all this is to the detriment of an effective hygiene.

Moreover the replacement of the floss after the first run would turn out to be scarcely practical, and also economically unacceptable.

Finally, both the devices described above present problems when used collectively, for instance in a family.

As a matter of fact, either the dental floss is completely replaced and that part of the device, which has to be introduced into the oral cavity of every user, is carefully cleaned, or it is necessary to provide a personal device for every single user, with a substantial increase in the expenses.

SUMMARY OF THE INVENTION

The objects of the present invention is to provide a device for supporting and operating a dental floss, suited to guarantee optimal conditions both from the hygienic and from the functional point of view.

Another object of the invention is to provide a device which, through some of its interchangeable parts, lends itself, easily and with a total safety of use and hygiene, to a collective use, thus reducing costs both on realization and on sale.

These objects are achieved by a technical solution simple and inexpensive to realize, which turns out to be easy and pleasant to use.

In particular the objects mentioned above are accomplished through a device for supporting and operating a dental floss, wherein said dental floss is made to run between the ends of the branches of a fork.

The device basically comprises: a rear part enclosed in a housing shaped in a hand grip, containing motor means connected with drive means coming out of said housing of said rear part, said motor means being suited to bring about a rotating motion and a swinging motion of said drive means; a front part coupled to a corresponding coupling zone provided on said rear part, and containing support means for supporting a dental floss, said support means engaging with said drive means to bring about the swinging advancement of said dental floss through an elongate section of said front part, ending with a fork, with a portion of said dental floss stretched between branches of said fork.

BRIEF DESCRIPTION OF THE DRAWINGS

The features of the invention will be further described hereinafter, with particular reference to the accompanying drawings, wherein:

FIG. 2 shows the device of FIG. 1 with its components separated from each other;

FIG. 2a is a perspective view of a detail of the device of FIG. 2, in a particular embodiment of the same detail;

FIGS. 3 and 4 show the device with its parts separated and viewed from above with removal of the upper parts to make the operating means of the same device visible;

FIG. 4a is a schematic view of the route of the dental floss in the device.

DESCRIPTION OF THE PREFERRED EMBODIMENT

Figure 1:
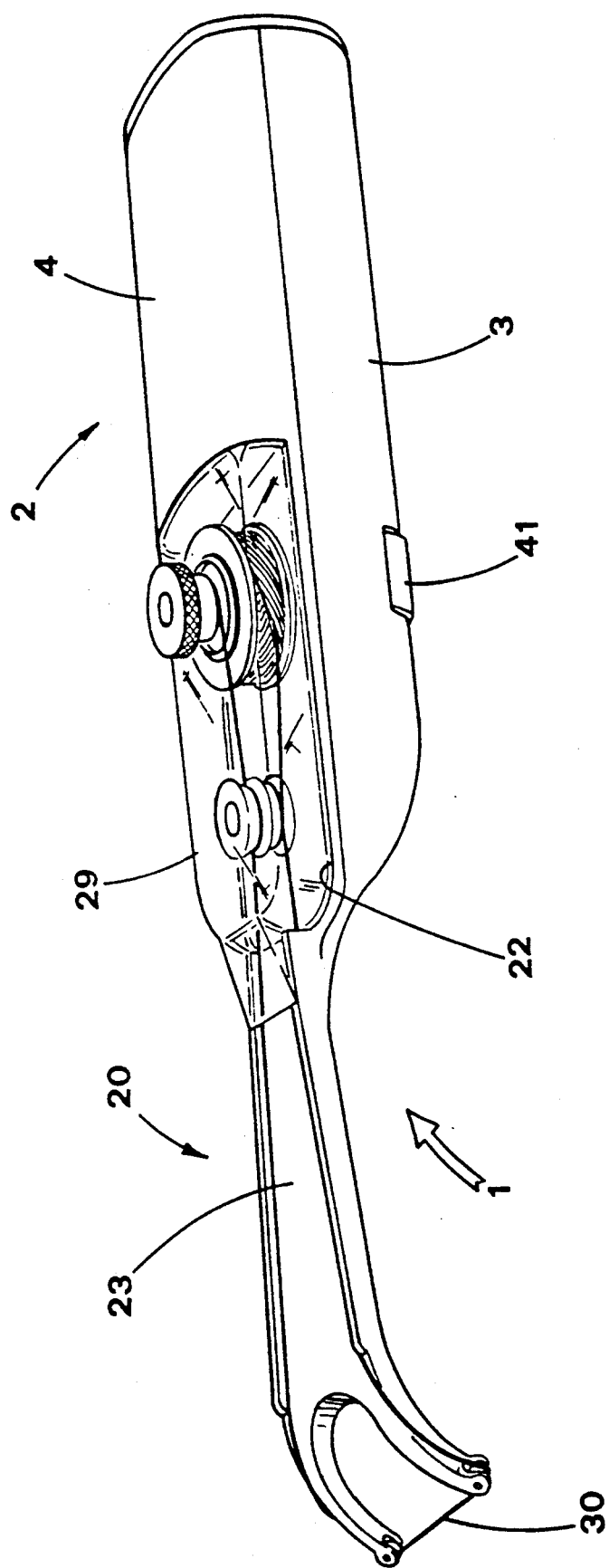
FIG. 1 is a perspective view of the device according to the invention.

With particular reference to the above-mentioned drawings, the numeral 1 generically designates the device for supporting and operating a dental floss 30.

The device 1 comprises a rear part 2 with the housing 3 shaped in a hand grip 4, containing motor means connected with drive means which come out of the housing.

The motor means comprise a small electric motor 5, housed in the rear zone of the housing 3, shaped in a hand grip 4.

The pinion 6 of the motor 5 engages with drive means consisting of a series of crown gears 7a, 7b, 7c, 7d, 7e, revolvingly supported by a plurality of vertical spindles 8a, 8b, 8c.

Each of the crown gears 7a, 7b, 7c, 7d, 7e, has two sections of different diameters, so as to be mutually cascade-connected. In other word the section of smaller diameter of the crown gear 7a engages with the section of larger diameter of the crown gears 7b, and so on.

The section of larger diameter of the first crown gear by 7a, as shown in FIG. 2, engages directly with the pinion 6 of the electric motor 5 while the last crown gear 7e is keyed to the first spindle 8a.

In this way, the first spindle 8a is driven into rotation when the motor 5 is activated, at a notably low speed (6-8 revs per minute).

A rocker element 9, revolvingly supported by the second spindle 8b with the axis of rotation parallel to the axis of the third spindle 8c, has an end 10 running along a cam 12 integral with the first crown gear 7a.

The cam 12 is obtained by means of a groove made on the upper side of the crown gear 7a.

The remaining end 11, bearing a toothing, engages with the third spindle 8c, through a sector gear 42 splined to said keyed, in order to impart it a swinging motion about its vertical axis.

In this way, the motor causes a motion of continuous rotation for the first spindle 8a, and a swinging motion for the third spindle 8c.

The first and third spindles come out of the housing 3 with one of their ends 8d, 8e; both ends 8d and 8e have a polygonal section.

The device 1 comprises also a front part 20 shaped at the rear complimentarily to a corresponding coupling zone 21 provided on said rear part 2.

The coupling zone 21 consists of a plane provided on the extension of the hand grip 4.

The front part 20 contains means to support a dental floss 30, which are able to engage with the drive means provided on the rear part 2, as described hereinafter.

The front part 20 may be subdivided into a box element 22, and an elongate section 23, ending with a fork 24.

The branches 25, 26 of the fork 24 are bent downwards and bear two small rollers 27 and 28 supported revolvingly.

Inside the box element 22 there are located the means to support the dental floss.

The box element 22 is closed by a cover 29, e.g. made removably integral with the same element through snap-fitting means of known type, or by other means, e.g. screws.

Inside the box element 22 there is located a reel 31, on which the dental floss 30 is wound up, revolvingly supported with its axis vertical.

Friction drive means are associated with the reel 31 and comprise a disk 34 coaxial with the reel and placed between this latter reel and the cover 29

One of the faces of the disk 34 rests against a corresponding head of the reel 31 and is provided with a circular relief fitting a circular seating made in the head of the reel 31, so as to hold the reel in the correct position.

A small tube 33 is made coaxially integral with the disk 34, on the opposite side as to the reel, in such a way that it comes out of the cover 29 through a hole 32.

Elastic means, consisting of a helical spring 35, are placed between the reel 31 and the bottom of the box element 22, so as to fit, at least partially, to a circular seating made in the lower head of the reel 31.

In this way the spring 35 pushes the reel 31 upward and keeps it against the disk 34 which in turn is pushed against the edge of the hole 32.

The spring 35, pressing the reel 31 against the disk 34, provides a friction system able to transmit motion, from the small tube 33 to the reel 31.

Inside the box element 22 there is also located a small roller 36, revolvingly supported with its axis vertical and featuring two circumferential races 37.

The dental floss runs into the two races 37 of the roller 36.

The small roller 36 is held in the correct position by a circular projection flat band 36a, coaxially integral to the lower head of the roller, that fits into a corresponding circular seating made in the bottom of the box element, while a protrusion 38, made in the cover 29, fits into a seating provided on the upper head of the small roller 36.

When the front part 20 is joined to the rear part, the end 8d of the spindle 8a, with polygonal section, passes through a hole made on the bottom of the box element 22, through the reel 31 and fits complimentarily into the small tube 33, engaging with this latter.

The end 8e of the spindle 8c, with polygonal section, fits complimentarily into the small roller 36, engaging with this latter.

A pawl 39 is screwed with the end 8d of the first spindle 8a, so as to press, through a truncated-cone element 40 screwed coaxially on the small tube 33, against the disk 34, locking the reel between the latter disk and the spring 35, thus making up the friction system.

As illustrated in FIG. 4, the dental floss 30, unwinding from the reel 31, is wound up for one or more turns around the small roller 36. Then the dental floss runs along the elongate section 23, until it comes out of the branch 26 of the fork 24, running in the groove of the small roller 28 positioned there.

Then, running in the groove of the other small roller 27, supported by the branch 25, the floss goes into this latter branch to run backwards in the elongate section 23.

Thus the dental floss 30 is wound one turn around the small roller 36 and thus it is locked with one end between the lower edge of the truncated-cone element 40, screwed on the small tube 33, and the corresponding surface of the disk 34, remaining locked there.

The spindle 8a, which passes through the small tube 33, rotates in a sense contrary to the unwinding sense of the floss from the reel 31, in such a way that the floss remains always stretched.

In particular, by screwing or unscrewing the pawl 39, the friction action of the small disk 34 on the reel is varied, since the load on the spring 35 changes, thus modifying also the stretch of the dental floss 30.

The floss winds up around the truncated-cone element 40 when the small tube 33 rotates.

When necessary, it is possible to unscrew the pawl to remove, by cutting, the dental floss 30 already used.

The floss stretch is not lost, as the spring 35, after that the pawl 39 has been unscrewed, presses the small disk 34 against the cover 29, thus locking the floss between the edge of the hole 32 and the upper surface of the small disk 34.

The small roller 36 is subjected to an oscillation of relatively high frequency about its vertical axis.

The oscillation obviously acts on the dental floss 30, thus bringing about the swinging advancement of the floss.

In this way the cleaning action of the dental floss is substantially improved, while concerning parts of floss continuously renewed.

The fork 24 may take the form which is every time most convenient; e.g. it may be smaller if the device is to be used by a child.

Alternatively, the two branches 25,26 may be straight and not bent downwards, as illustrated in the drawings.

The activation of the small motor 5 is provided through a switch 41, located in a suitable position on the hand grip 4, and connected with an external feeder through a wire.

In another form the power cord has a RF generator connected to a RF coil surrounding a socket, while the device has a profile so as to be inserted into the socket.

In the part inserted in the socket, the device is provided with a RF coil connected to one or more batteries.

This way the device can be coupled to the feeder without the conventional power cord and can be freely used once it has been taken out from the socket.

With the present device, hygienic safety is totally guaranteed, since the dental floss, after having been delivered by the first reel 31 and wound up on the truncated-cone element 40 is eliminated every time, thus avoiding any repeated use.

In other words, the dental floss runs only once among the teeth, but at such a speed that the consumption of the floss is made economically acceptable, while achieving optimal results also from the functional point of view.

Furthermore, the device is well suitable for a collective use, e.g. in a family.

In fact, it is sufficient to provide a front part 20 for each user and a single rear part 2, to which every user will attach his own front part 20 when required.

In order to optimize the replacement of the front part of the device, and to reduce manufacturing costs and user costs further, it is possible to provide for the splitting of the same front part, in one of its intermediate points.

As it is illustrated by way of example in FIG. 2a, and outlined by a broken line in FIG. 2, the front part 20 may be split immediately downstream of the fork 24.

Locking means 44 (of known type, such as snap pins or else) make it possible to provide the fastening of the fork to the front part 20.

Therefore, the fork may be replaced by every user, or for every single user, thus bringing about a subsequent advancement of the floss 30, which is brought with a new segment, not used previously, close to the fork just replaced.

It stands to reason that the fork made according to this latter embodiment will be shaped in such a way as to be able to receive the floss 30 into a special open channel 45, in order to allow said floss to be mounted without having to be necessarily extracted.

It is understood that the above has been described by way of example and it is not restrictive, therefore any other possible embodiment of the device conforming to the invention is to be considered as covered by the patent hereby applied for, as described above and as claimed hereinafter.

What is claimed is:

1. A device e for supporting and operating a dental floss comprising:
   a rear pat enclosed in a housing shaped with a hand grip and containing motor means having a rotating pinion and drive means of said housing;
   a front part coupled with a corresponding coupling zone of said rear part and having means for supporting a roll of dental floss, said front part having an elongate section terminating in a fork with said dental floss extending from said roll and along said elongated part and having a portion stretched between branches of said fork;
   said drive means located in said rear part to engage said motor pinion comprising:
   a series of cascade-connected crown gears rotatably supported by a plurality of vertical spindles, each of said crown gears having two sections of different diameter, with a section of smaller diameter of each crown gear engaging with a section of larger diameter of a subsequent crown gear, a section of larger diameter of a first crown gear engaging with said motor pinion while a last crown gear is keyed onto a first spindle to dive the same first spindle into axial rotation; and
   a rocker element rotatably supported by a second spindle and having an end engaging with a cam integral with one of said crown gear and having the other end engaging with a third spindle to bring about a swinging motion about a vertical axis of said third spindle.

2. A device as in claim 1 wherein said first spindle and third spindles each have an cam projecting out of said housing, an end of one of said first and third spindles having a polygonal section.

3. A device as in claim 1, wherein said cam is formed by a groove on a side of one of said crown gears.

4. A device as in claim 1, wherein said rocker element is supported with the axis of rotation parallel to the axis of said third spindle to which is coupled to the other end of said rocker element, said rocker element other end having a tooth engaging with a sector gear splined to said thick spindle.

5. A device as in claim 1, wherein said rear art serves as a hand grip and surface formed on an extension of said hand grip to serve as a coupling for said front and rear parts.

6. A device as in claim 1, when said support means, engaging with said drive means comprise:
   a reel on which said dental floss is wound supported with its axis vertical;
   friction drive means acting on said reel;
   means to lock an end of said dental floss to drive the floss;
   said dental floss running through an elongated section of said front part and exiting from one of said fork branch and entering through the other branch;
   a roller having two circumferential spaced races rotatably supported with its axis vertical to engage said drive means, and receiving in each of said races, a corresponding portion of dental floss to impart a swinging motion to said floss.

7. A device according to claim 6, wherein said friction drive mean comprises:

a small disk mounted coaxially between said reel and a cover, said reel having one of its faces resting against a corresponding head of said reel and with a tubular member integral therewith for receiving in a complementary coupling the part of said drive mean extending from said rear part;

elastic means mounted coaxially between said reel and the bottom of a box element for pressing said reel against said small disk to provide a friction contact to transmit motion from said tubular member to said reel;

a pawl for engaging the part of said drive means projecting from said rear part to press, through a truncated-cone element mounted coaxially to and against said disk locking said reel said elastic means to impart to said reel a tendency to rotate counter to the unwinding direction of the flow so as to keep said floss stretched and to drive said locking means into rotation.

8. A device according to claim 7, wherein said disk also locks the dental floss when said pawl is disengaged from said part of said drive means projecting from said a rear part, locking said floss between its upper surface and the edge of said hold provided on said cover, to allow the cuting of the portion of said dental floss already used while keeping the remaining floss stretched.

9. A device according to claims 6, wherein said locking means comprises said small disk and said truncated-cone element for locking an end of the dental floss between the lower edge of said truncated-cone element and the corresponding surface of said small disk, to drive said dental floss.

10. A device according of claim 6, further comprising a roller held in position by a flat band coaxially provided on its lower head in a corresponding seating made on the bottom of a box element, while provision is made for a protrusion made in said cover and fitting a corresponding seating provided on the upper head of said roller.

11. A device according to claim 6, wherein the ends of said fork branches are bent downwards, and each has a small roller at its end on which said dental flows runs.

12. A device according to claim 6, wherein said front part to which said fork is fastened has an open channel inside which said dental floss runs.

* * * * *